United States Patent
Cooney, III et al.

(10) Patent No.: US 6,709,459 B1
(45) Date of Patent: Mar. 23, 2004

(54) RADIAL IMPLANT SYSTEM

(75) Inventors: William P. Cooney, III, Rochester, MN (US); Bernard F. Morrey, Rochester, MN (US); Shawn W. O'Driscoll, Rochester, MN (US); Ronald L. Linsheid, Rochester, MN (US); David A. Leibel, Princeton, MN (US); Fredrick M. Schultz, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 0 days.

(21) Appl. No.: 09/652,872

(22) Filed: Aug. 31, 2000

(51) Int. Cl.[7] ................................................. A61F 2/38
(52) U.S. Cl. ................................................. 623/20.11
(58) Field of Search ........................... 623/16.11, 18.11, 623/19.13, 19.14, 20.11, 21.11, 21.12, 21.15, 21.18, 21.19, 23.11, 23.12; 606/96, 102

(56) References Cited

U.S. PATENT DOCUMENTS

| | | | |
|---|---|---|---|
| 3,593,342 A | | 7/1971 | Neibauer |
| 3,875,594 A | | 4/1975 | Swanson |
| 4,178,640 A | | 12/1979 | Buechler |
| 4,242,759 A | | 1/1981 | White |
| 4,936,854 A | * | 6/1990 | Swanson ................. 623/20.11 |
| 4,944,758 A | | 7/1990 | Bekki |
| 5,037,440 A | | 8/1991 | Koenig |
| 5,522,900 A | | 6/1996 | Hollister |
| 5,782,923 A | * | 7/1998 | Engelbrecht ............. 623/20.11 |
| 5,879,395 A | * | 3/1999 | Tornier ..................... 623/20.11 |
| 6,027,534 A | * | 2/2000 | Wack ....................... 623/20.11 |
| 6,096,084 A | * | 8/2000 | Townley .................. 623/23.12 |
| 6,173,200 B1 | * | 1/2001 | Cooke ........................ 600/425 |
| 6,193,724 B1 | * | 2/2001 | Chan .......................... 606/102 |
| 6,217,616 B1 | * | 4/2001 | Ogilvie .................... 623/20.11 |
| 6,224,634 B1 | * | 5/2001 | Keller ....................... 623/23.11 |
| 6,270,529 B1 | * | 8/2001 | Terrill-Grisoni ......... 623/20.11 |
| 6,306,171 B1 | * | 10/2001 | Conzemius ............... 623/18.11 |

* cited by examiner

Primary Examiner—Paul B. Prebilic
Assistant Examiner—William H. Matthew
(74) Attorney, Agent, or Firm—Patterson, Thuente, Skaar & Christensen, P.A.

(57) ABSTRACT

A prosthesis for the radius bone in the arm of a patient includes a head shaped for engagement with the capitellum of a humerus bone and the radial notch of the ulna. It also has a curved stem that extends from the head and is tapered with a distally decreasing cross section for insertion into the medullary canal of the radius. A system for implanting the prosthesis requires a resection guide for placing the forearm of the patient in a precise anatomical orientation for resection of the radius bone. The resection guide includes a notched alignment rod attached to an adjustable flange and a reference flange for aligning the forearm for a cut of the radius bone perpendicular with the axis of rotation of the radius bone about the ulna, and for measuring the size of the resection and prosthesis.

21 Claims, 2 Drawing Sheets

RADIAL IMPLANT SYSTEM

FIELD OF THE INVENTION

The present invention pertains generally to prostheses. More specifically, the present invention pertains to prostheses which act as part of an elbow joint in a patient for motions which mimic anatomical movements. The present invention is particularly, but not exclusively, useful as a prosthesis for the radial head in the elbow joint of a patient.

BACKGROUND OF THE INVENTION

Like other joints and anatomical features of the human body, the elbow joint is exceedingly complex in its make-up and function. Also like the other joints and anatomical features of the human body, the elbow joint is unique unto itself and requires specific consideration for its reconstruction or replacement. The complexity and uniqueness of this joint are quite interesting and are, perhaps, best appreciated by considering the skeletal motions which are involved in its movement.

In the transition of the hand and forearm from pronation to supination the radius and ulna of the forearm transition from a crossed relationship to a side-by-side relationship. Thus, in this movement there is a relative rotation of the radius bone about the ulna. Also, but more subtly, during the transition between pronation and supination there is also some relative translational movement between the radius bone and the ulna. The consequence of all this is that from a reference point on the ulna, the radius bone appears to move with a general motion that includes both translation and rotation. The head of the radius interacts with the capitellum and the radial notch of the ulna during pronation and supination, providing elbow and forearm stability during rotation and translation.

In addition to its importance as a component of forearm function, the radial head is an equally important component of normal elbow function. Indeed, elbow function involves bending, lifting and twisting movements, all of which require joint stability. Because motions in the human body require the interaction of various anatomical components, it is crucial that replacement of a component be precise in form, size, and orientation. While the head of the radius bone directly engages the capitellum of the humerus and the radial notch of the ulna, it also relates indirectly to other anatomical components of the arm. Specifically, ligaments surrounding the radial head are essential to elbow stability. Further, misalignment of the radius bone will cause poor radial-capitellar joint contact, leading to subluxation, or poor alignment of the elbow. It follows that the wrist and shoulder joints are also affected by the alignment of the radius bone.

The importance of having a workable prosthesis for the head of the radius bone is underscored by the debilitating effects which commonly result when a joint becomes damaged due to fracture, arthritis, or osteochondrosis. It is well known that radial head resection, as seen in elbow injuries, results in persistent elbow instability. Additionally, forearm axial instability can result from radial head excision if the remaining stabilizers, the supporting ligaments, are compromised. Because this loss of stability affects the interdependent functions of the elbow and forearm, when the radial head is damaged, it is common to see further damage to other components of the radial ulnar joint system, including, but not limited to, the complex system of supporting ligaments that encase the elbow joint. It has been well demonstrated that damage of any one of the components of the radial ulnar joint system leads to pain, weakness, and loss of motion. It is, therefore, of great importance to the patient that damage to the radial head be remedied.

In light of the above, it is an object of the present invention to provide a prosthesis for engaging a radius bone in the forearm of a patient with the capitellum of a humerus bone and the radial notch of the ulna at the elbow of a patient. It is a further object of the present invention to provide a prosthesis that is shaped to establish a secure engagement with the radius bone and is capable of cooperating with the anatomic structure and function of the portion of the radius being replaced. Yet another object of the present invention is to provide a system for implanting the prosthesis which places the forearm in the precise anatomical orientation necessary for implantation of the prosthesis. It is also an object of the present invention to precisely measure the length of the radial bone to be resected, and to precisely measure the size of the prosthesis to be implanted in place of the resected bone. Another object of the present invention to provide a prosthesis that is relatively easy to manufacture, is simple to implant, and is comparatively cost effective.

SUMMARY OF THE PREFERRED EMBODIMENTS

In accordance with the present invention, a prosthesis for replacing the head of a radius bone in the elbow of a patient includes a head and a curved stem which extends therefrom. Specifically, the head is shaped for simultaneous articulation with both the capitellum of the humerus bone and with the radial notch of the ulna. Also, the stem is curved, or arcuate shaped, in order to accommodate the anatomy of the proximal radius after resection of the radial head, and to securely anchor the prosthesis when the stem is inserted into the medullary canal of the radius bone.

In detail, the head of the prosthesis of the present invention has a proximal surface that is formed as a substantially concave recess, and it has a distal surface that is formed with a hole. Preferably, the proximal surface of the head is made of highly polished cobalt chrome or a ceramic material to facilitate articulation of the head with the capitellum and with the radial notch of the ulna bone. More specifically, as envisioned for the present invention this articulation involves a relative sliding motion between the head of the prosthesis and both the capitellum and the radial notch of the ulna.

The stem of the prosthesis has a proximal end and a distal end. Also, the stem is preferably made of a material such as cobalt chrome or titanium. Further, it has an extension at its proximal end that is slightly tapered with a proximally decreasing cross section to facilitate insertion of the extension into the hole in the distal surface of the head. Preferably, the extension is configured as a morse taper. In any event, as intended for the present invention, the proximally decreasing cross section of the extension establishes an interference fit between the extension of the stem and the head that helps to hold the head on the stem.

As indicated above, the stem of the prosthesis is curved in shape and is generally arcuate. Importantly, the configuration of the stem is intended to structurally mimic the shape of the medullary canal of the radius bone. In general, to accomplish this the stem is formed with a first portion and a second portion. Specifically, the first portion is attached to the head and extends distally therefrom substantially along a first axis. The second portion then extends distally from the first portion substantially along a second axis. In their relation to each other, the first axis and the second axis define an angle α therebetween. Preferably, the angle α will be in a range of about 5 degrees to approximately 25 degrees. The curve of the stem that is established by the angle α can be achieved using a radius of curvature that is in a range of about 0.5 inch to approximately 3 inches. Further, as it extends distally along the first and second axes, the stem is tapered with a distally decreasing cross section. This facilitates insertion of the stem into the medullary canal of the radius bone and helps to anchor the prosthesis on the radius bone. The stem also has a roughened or textured surface, which interacts with the medullary canal of the radius bone to help hold the stem on the radius. For purposes of the present invention, the surface of the stem can be coated with a material such as titanium, cobalt-chrome beads or hydroxyapatite. In addition to these structural features, the stem also has a collar that is formed on the first portion of the stem. As intended for the present invention, this collar is positioned to limit insertion of the stem into the medullary canal.

In order to implant the prosthesis of the present invention into the radius bone of a patient, it is first necessary to do a resection of the radius by removing the radial head and exposing the medullary canal. When doing this, it is important that the prosthesis have the same functional dimensions as the amount of bone that is to be removed. For the present invention, the required accuracy for this exchange is achieved by using a resection guide.

In accordance with the present invention, the resection guide includes an alignment rod which has a series of notches on its surface near the proximal end. The resection guide also includes an adjustable flange and a reference flange. Specifically, the reference flange is pre-positioned at a fixed location between the distal and proximal ends of the alignment rod. When the adjustable flange is engaged with the alignment rod, it can be selectively fixed at one of the notches on the alignment rod.

As intended for the present invention, the notches on the alignment rod are located relative to the reference flange so that, when the adjustable flange is affixed to the alignment rod, the distance between the adjustable flange and the reference flange will correspond with a particular head size of the prosthesis. Thus, upon the engagement of the adjustable flange with a notch, the size of the head of the prosthesis can be determined.

For the operation of the resection guide, after an incision has been made to establish access into the elbow of the patient, the adjustable flange is engaged with the proximal end of the alignment rod. The adjustable flange is then positioned against the articular surface of the capitellum. Also, the distal end of the alignment rod is positioned over the ulna styloid process. When so positioned, the alignment rod establishes the axis of rotation of the radius about the ulna. Stated differently, the adjustable flange is oriented to align the alignment rod with the center of rotation of the capitellum and with the styloid of the ulna. Next, once the alignment rod is properly positioned between the capitellum and the styloid of the ulna, the alignment rod and the reference flange that is attached to the alignment rod are guided proximally or distally relative to the adjustable flange until the adjustable flange is located at a notch on the alignment rod and the reference flange is positioned at a desired location on the radius. At this point, the reference flange is positioned to establish a distance between the adjustable flange and the reference flange that is equal to a desired length for radial head resection.

As the alignment rod is guided to position the reference flange at a desired location on the radius for resection, the distal end of the alignment rod is simultaneously positioned at the styloid process of the ulna. Thus, the forearm of the patient is positioned for an osteotomy in a plane that is substantially perpendicular to the axis of rotation of the radius bone about the ulna. In this position, the reference flange can be used as a guide to establish a cutting line for the resection. Specifically, the reference flange will guide the cutting of the radius in a plane that will be perpendicular to the axis of rotation of the radius bone about the ulna. The cut thus made to the radius bone will facilitate insertion of the curved stem of the prosthesis into the medullary canal of the radius bone.

Once the radial head has been removed, it can be replaced by the prosthesis. Specifically, this is done by inserting the stem of the prosthesis into the medullary canal and positioning the head of the prosthesis on the stem for articulation with the capitellum and the ulnar notch.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

DESCRIPTION OF THE PREFERRED EMBODIMENT

Figure 1:
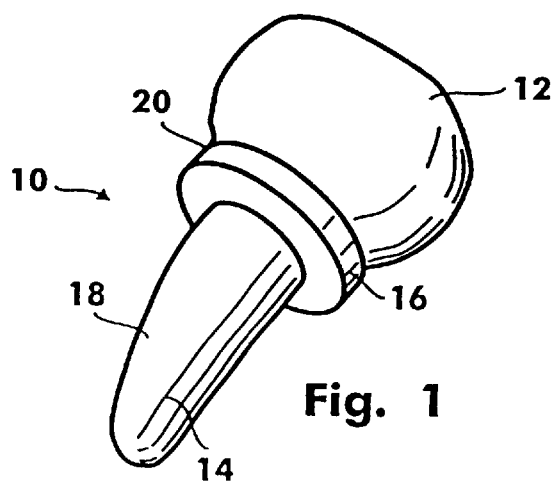
FIG. 1 is a perspective representation of the prosthesis.

A prosthesis in accordance with the present invention is shown in FIG. 1 and is generally designated 10. As shown, the prosthesis 10 essentially includes a head 12 and a curved stem 14. For the purposes of the present invention, the curved stem 14 is made of a material such as cobalt chrome or titanium. Further, the prosthesis 10 includes a collar 16 that is integral with the stem 14. Preferably, both the surface 18 of the stem 14 and the surface 20 of collar 16 are roughened, or textured. For the purpose of this invention the surface 20 of the stem 14 and collar 16 can be coated with a material such as titanium, cobalt-chrome beads, or hydroxyapatite. For purposes of this disclosure, and specifically for relative directional references between components of the present invention, the head 12 is considered to be proximal to the stem 14. Accordingly, the stem 14 is considered to be distal to the head 12.

Figure 2:
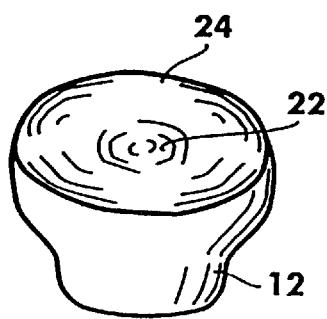
FIG. 2 is a perspective view of the head of the prosthesis.
Figure 3A:
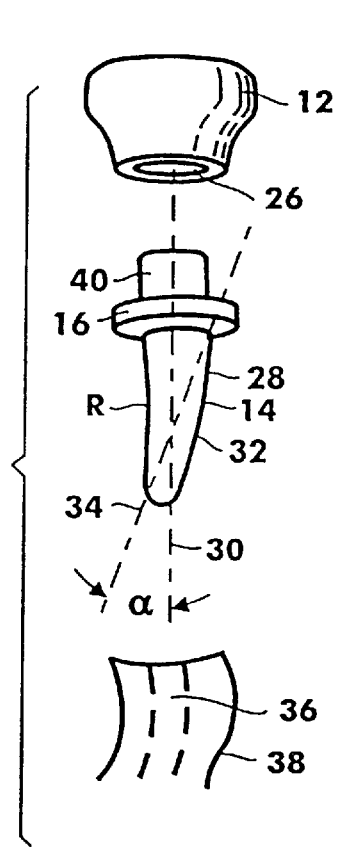
FIG. 3A is an exploded elevation view of the head of the prosthesis and the stem of the prosthesis positioned for insertion into the medullary canal of a radius bone.

In FIG. 2 it can be seen that the head 12 is formed with a recess 22, and that the recess 22 is generally concave in shape. For the purposes of the present invention the head 12, and particularly the proximal surface 24 of recess 22, is made of a highly polished cobalt chrome or a ceramic material. In FIG. 3A, it can be seen that the head 12 is also formed with a distal hole (i.e. bore) 26 that is on the opposite side of the head 12 from the recess 22.

Still referring to FIG. 3A, the structure of stem 14 for the present invention is seen to generally include two distinct portions. A first (proximal) portion 28 is substantially aligned along an axis 30. Also there is a second (distal) portion 32 that is substantially aligned along an axis 34. An angle, α, is formed between the axis 30 and the axis 34 which gives the stem 14 a curved or arcuate appearance. For an alternate description of the stem 14, it can be noted that the second portion 32 of the stem 14 is bent relative to the first portion 28. Specifically, as shown in FIG. 3A, at the transition between the first portion 28 and the second portion 32, there is an effective radius of curvature, R, which will establish the particular configuration for the stem 14.

In addition to the curved or arcuate configuration for the stem 14, it is to be appreciated that the stem 14 is tapered with a distally decreasing cross section. Further, as shown in FIG. 3A, the stem 14 includes an extension 40 that is actually the part of first portion 28 that extends proximally from the collar 16. As intended for the present invention, the extension 40 can be slightly tapered with a proximally decreasing cross section. The purpose of the tapered extension 40 is to facilitate the engagement of the stem 14 with the head 12.

Regardless whether the curved or arcuate configuration for the stem 14 is described in terms of the angle "α," or the radius of curvature "R," and regardless of the amount of taper provided for the stem 14 or the extension 40, it is important that the resulting configuration for the stem 14 effectively conform to the medullary canal 36 of the radius bone 38. For the present invention, this means that the angle α will be generally in a range from about five degrees to approximately twenty-five degrees (α=between 5° and 25°). The curve of the stem 14 that is established by the angle α can be achieved using a radius of curvature that is in a range of about 0.5 inch to approximately 3 inches.

Figure 3B:
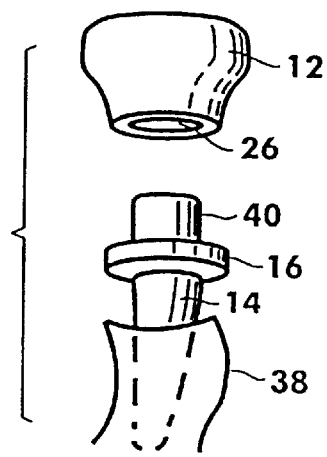
FIG. 3B is an exploded side elevation view showing the stem of the prosthesis inserted into the medullary canal of a radius bone.
Figure 3C:
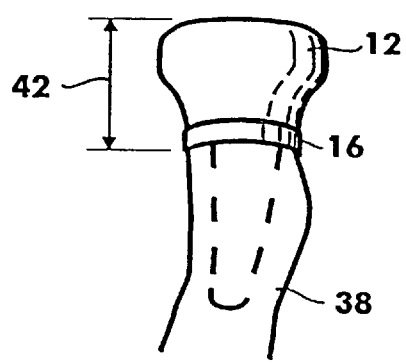
FIG. 3C is a side elevation view of the prosthesis after implantation into the radius bone.

The actual engagement of the prosthesis 10 with a radius bone 38 will, perhaps, be best appreciated by collectively considering FIGS. 3A, 3B and 3C. When doing this it is to be appreciated that the radius bone 38 has previously been resectioned. Further, it will be noted that the configuration for stem 14 is chosen to establish an interference, or friction fit with the radius bone 38. Preferably, this can be done without using cement. If necessary, however, the present invention envisions that a cement of a type well known in the pertinent art can be used to anchor the stem 14 in the medulilary canal 36 of the radius bone 38. Once the stem 14 has been engaged with the radius bone 38 (FIG. 3B), the head 12 can then be engaged with the stem 14 (FIG. 3C). Specifically, engagement of the head 12 onto the stem 14 is done by simply inserting the extension 40 of the stem 14 into the hole 26 of the head 12. The result is that the head 12 will extend from the radius bone 38 through a distance 42.

Figure 4:
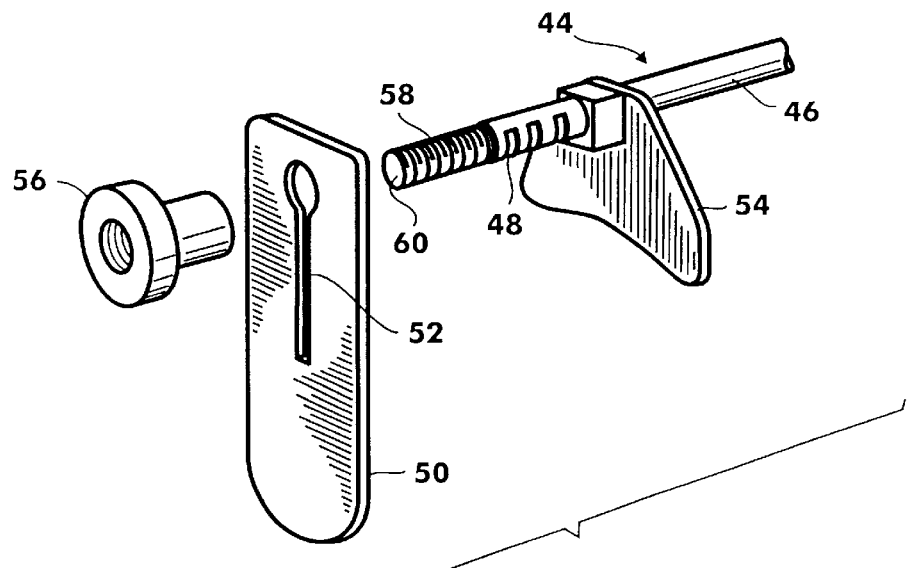
FIG. 4 is an exploded perspective view of a portion of the resection guide of the present invention.
Figure 5:
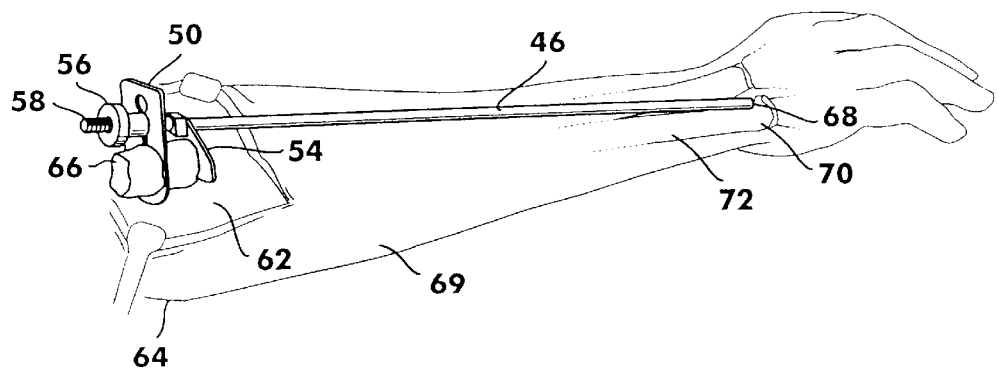
FIG. 5 is a perspective view of the resection guide of the present invention in position on the forearm of a patient for performing a resection of the radial head.

It is an important aspect of the present invention that the distance 42 through which the head 12 extends from the radius bone 38 be anatomically correct. To ensure this, the present invention envisions the use of a resection guide such as the one shown in FIG. 4 and generally designated 44. As shown, the resection guide 44 includes an alignment rod 46 which is formed with a plurality of notches 48 near its proximal end 60 (the specific notches 48 a–c are only exemplary). The resection guide 44 also includes an adjustable flange 50 that is formed with a slot 52 and it includes a reference flange 54 that is pre-positioned at a fixed location between the notches 48 and the distal end 68 of the alignment rod 46. Further, when a notch 48 on the alignment rod 46 is inserted through the slot 52 of the adjustable flange 50, the nut 56 can be engaged with the thread 58 at the proximal end 60 of the alignment rod 46 to fixedly hold the adjustable flange 50 to the alignment rod 46. As intended for the present invention, the notches 48 are located relative to the reference flange 54 so that, when the adjustable flange 50 is affixed to the alignment rod 46, the distance between the adjustable flange 50 and the reference flange 54 will correspond with a particular head 12 size of the prosthesis 10. Thus, upon the engagement of the adjustable flange 50 with a notch 48, the size of the head 12 of the prosthesis 10 can be determined.

For the operation of the resection guide 44, the resection guide 44 is initially assembled as described above. After an incision 62 has been made to establish access into the elbow 64 of a patient, the adjustable flange 50, is positioned against the capitellum 66. The alignment rod 46 with the reference flange 54 attached, is then engaged with the adjustable flange 50. Next, the alignment rod 46 and attached reference flange 54 are guided proximally or distally relative to the adjustable flange 50 which is located at a notch 48 on the alignment rod 46 until the reference flange 54 is positioned at a desired location on the radius 38. At this point, the reference flange 54 is positioned to establish a distance between the adjustable flange 50 and the reference flange 54 that is equal to a desired length for a radial head resection.

While the alignment rod 46 and attached reference flange 54 is guided to position the reference flange 54 at a desired location on the radius 38 for resection, the distal end 68 of the alignment rod 46 is positioned over the ulna styloid process 70. Thus, the forearm 69 of the patient is positioned for an osteotomy in a plane that is perpendicular to the axis of rotation of the radius bone 38 about the ulna 72. In this position, the reference flange 54 can be used as a guide to establish a cutting line for the resection. Specifically, close to the position of the resection guide 44, the reference flange 54 will guide the cutting of the radius 38 in a plane that will be perpendicular to the axis of rotation of the radius bone 38 about the ulna 72.

As intended for the present invention, the spacing between the adjustable flange 50 and the reference flange 54 will determine the distance 44 for the prosthesis 10. Stated differently, when resection of the radius bone 38 is accomplished at the reference flange 54, the amount of radius bone 38 that is removed will be precisely known. Importantly, this removed bone must be compatible with the prosthesis 10 that is to be implanted. Furthermore, the cut on the radius bone 38 has been made so that the curved stem 14 of the prosthesis 10 can then be engaged with radius bone 38 as disclosed above with reference to FIGS. 3A, 3B and 3C.

While the particular Radial Implant System as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

What is claimed is:

1. A prosthesis for engaging a radius bone in a forearm of a patient with the capitellum of a humerus bone and the radial notch of the ulna at the elbow of the patient, said prosthesis comprising:

a head formed with a surface shaped for engagement with the capitellum to allow for a relative sliding motion therebetween; and a stem attached to said head having a proximal end and a distal end, said stem having a first portion extending distally from said proximal end and substantially along a first axis, and having a second portion extending distally from said first portion and substantially along a second axis to said distal end, said first axis and said second axis defining an angle α therebetween, said stem being shaped to facilitate insertion of said stem into the medullary canal of the radius bone to anchor said prosthesis on the radius bone.

2. A prosthesis as recited in claim 1 wherein said angle α is a range between 5 degrees and 25 degrees.

3. A prosthesis as recited in claim 1 wherein the transition between said first portion and said second portion has a radius of curvature in a range between about 0.5 inches and approximately 3 inches.

4. A prosthesis as recited in claim 1 wherein said head has a proximal end and a distal end, said distal end of said head being formed with a hole and said first portion of said stem being formed with an extension for insertion into said hole of said head to connect said stem to said head.

5. A prosthesis as recited in claim 4 wherein said proximal end of said head is formed as a concave recess.

6. A prosthesis as recited in claim 4 wherein said stem has a collar positioned on said first portion of said stem to limit insertion of said stem into the medullary canal of the radius bone, and wherein said extension of said stem is tapered with a proximally decreasing cross section to facilitate insertion of said extension into said hole in said head, and to establish an interference fit between said extension and said head.

7. A prosthesis as recited in claim 1 wherein said stem has a roughened surface, for interaction with the medullary canal of the radius bone.

8. A prosthesis as recited in claim 1 wherein said surface of said head is made of a highly polished cobalt chrome to facilitate articulation of the radius bone with the capitellum and with the radial notch of the ulna.

9. A system for implanting a prosthesis into an elbow of a patient to engage a radius bone in the forearm of the patient with the capitellum of the humerus bone and the ulnar notch of the patient which comprises:
   a prosthesis having a head and a stem, said stem having a proximal end and a distal end, said stem having a first portion extending distally from said proximal end and substantially along a first axis, and having a second portion extending distally from said first portion and substantially along a second axis to said distal end, said first axis and said second axis defining an angle α therebetween, said stem being shaped for insertion into the medullary canal of the radius bone; and
   a means for placing the forearm of the patient in an anatomical orientation for resection of the radius bone to expose the medullary canal of the radius, said placing means including a means for guiding a cutting blade during resection of the radius bone to cut the radius bone in a plane, said plane being substantially perpendicular to an anatomical axis of rotation of the radius about the ulna.

10. A system as recited in claim 9 wherein said stem is tapered with a distally decreasing cross section to facilitate insertion of said stem into the medullary canal of the radius bone to anchor said prosthesis on the radius bone.

11. A system as recited in claim 9 wherein said head is formed with a surface shaped for engagement with the capitellum to allow for a relative sliding motion therebetween, said surface of said head being made of a highly polished cobalt chrome to facilitate articulation of the radius bone with the capitellum and with the radial notch of the ulna bone.

12. A system as recited in claim 11 wherein said head has a proximal end and a distal end, and wherein said distal end is formed with a hole and said first portion of said stem is formed with an extension for insertion into said hole to connect said stem to said head.

13. A system as recited in claim 12 wherein said proximal end of said head is formed as a concave recess.

14. A system as recited in claim 12 wherein said stem has a collar positioned on said first portion of said stem to limit insertion of said extension of said stem into said hole in said head, and to limit insertion of said stem into the medullary canal of the radius bone.

15. A system as recited in claim 12 wherein said extension of said stem is tapered with a proximally decreasing cross section to facilitate insertion of said extension into said hole in said head, and to establish an interference fit between said extension and said head.

16. A system as recited in claim 9 wherein said stem has a roughened surface, for interaction with the medullary canal of the radius bone.

17. A system for implanting a prosthesis into an elbow of a patient to engage a radius bone in the forearm of the patient with the capitellum of the humerus bone and the ulnar notch of the patient which comprises:
   a prosthesis having a head and a stem, said stem having an arcuate shape for insertion into the medullary canal of the radius bone;
   an alignment rod having a proximal end and a distal end, a reference flange fixedly positioned between said proximal end and said distal end of said alignment rod, said reference flange being positioned on the radius bone with said distal end of said alignment rod positioned on the styloid process of the ulna in the forearm of a patient to orient the forearm of the patient for resection; and
   an adjustable flange slidingly positioned on said alignment rod proximal to said reference flange to establish a length of the radius bone between said reference flange and said rotating flange for resection, said reference flange being used for guiding a cutting blade during resection of the radius bone to cut the radius bone in a plane, said plane being substantially perpendicular to the anatomical axis of rotation of the radius about the ulna.

18. A system as recited in claim 17, wherein said adjustable flange is formed with a slot for receiving said alignment rod, said adjustable flange having a first and a second surface, wherein said first surface of said adjustable flange is placed against the capitellum to anchor said alignment rod during resection of the radius.

19. A system as recited in claim 17 wherein said alignment rod has a plurality of notches extending distally from said adjustable flange, each respective said notch establishing a size of said prosthesis for implantation into the radius bone when said adjustable flange is positioned thereon.

20. A system as recited in claim 17 wherein said reference flange has a proximal surface and a distal surface, and wherein said distal surface guides a cutting blade for resection of the radius bone.

21. A method for replacing the head of the radius bone with a prosthesis, said method comprising the steps of:
   providing a prosthesis having a head and a stem, said stem having a proximal end and a distal end, said stem having a first portion extending distally from said proximal end and substantially along a first axis, and having a second portion extending distally from said first portion and substantially along a second axis to said distal end, said first axis and said second axis defining an angle α therebetween;

incising the forearm of a patient to expose the radius bone at the elbow of the patient;

fixing the capitulum and the styloid process of the ulna in a precise anatomical orientation for removal of a portion of the radius bone and insertion of said prosthesis;

resecting a measured length of the radius bone;

determining the exact size of said prosthesis to correspond with the measured length of the resected portion of the radius bone;

preparing a measured portion of the medullary canal of the radius bone to receive said stem of said prosthesis;

inserting said stem of said prosthesis into the medullary canal of the radius bone;

attaching said head of said prosthesis to said stem of said prosthesis; and suturing the incision.

\* \* \* \* \*

UNITED STATES PATENT AND TRADEMARK OFFICE
CERTIFICATE OF CORRECTION

PATENT NO. : 6,709,459 B1
DATED : March 23, 2004
INVENTOR(S) : William P. Cooney, III et al.

It is certified that error appears in the above-identified patent and that said Letters Patent is hereby corrected as shown below:

<u>Column 7,</u>
Lines 1 and 44, insert -- length defined by a -- between "a" and "proximal".
Lines 2 and 44, replace "distal end," with -- distal end with a smooth continuous surface therebetween, --.
Lines 4 and 46, replace "first axis," with -- first axis to about the middle of said stem length, --.

<u>Column 8,</u>
Line 66, insert -- length defined by a -- before "proximal end".
Line 66, replace "distal end," with -- distal end with a smooth continuous surface therebetween, --.

<u>Column 9,</u>
Line 1, replace "first axis," with -- first axis to about the middle of said stem length, --.

Signed and Sealed this

Twenty-seventh Day of July, 2004

JON W. DUDAS
*Acting Director of the United States Patent and Trademark Office*